(12) United States Patent
Itoh et al.

(10) Patent No.: US 8,865,423 B2
(45) Date of Patent: Oct. 21, 2014

(54) METHOD AND KIT FOR QUANTITATIVELY DETERMINING SMALL, DENSE LDL CHOLESTEROL

(71) Applicant: Denka Seiken Co., Ltd., Tokyo (JP)

(72) Inventors: Yasuki Itoh, Niigata (JP); Miki Fujimura, Niigata (JP)

(73) Assignee: Denka Seiken Co., Ltd., Tokyo (JP)

(*) Notice: Subject to any disclaimer, the term of this patent is extended or adjusted under 35 U.S.C. 154(b) by 0 days.

(21) Appl. No.: 13/860,435

(22) Filed: Apr. 10, 2013

(65) Prior Publication Data

US 2013/0288281 A1 Oct. 31, 2013

Related U.S. Application Data

(62) Division of application No. 12/682,240, filed as application No. PCT/JP2008/068489 on Oct. 10, 2008, now Pat. No. 8,440,419.

(51) Int. Cl.
- *C12Q 1/60* (2006.01)
- *C12N 9/14* (2006.01)
- *G01N 33/92* (2006.01)

(52) U.S. Cl.
CPC . *C12Q 1/60* (2013.01); *G01N 33/92* (2013.01)
USPC .......................................................... 435/11

(58) Field of Classification Search
None
See application file for complete search history.

(56) References Cited

U.S. PATENT DOCUMENTS

| | | | |
|---|---|---|---|
| 2001/0031479 A1* | 10/2001 | Miyauchi | 435/11 |
| 2006/0154374 A1 | 7/2006 | Itoh et al. | |
| 2009/0023167 A1 | 1/2009 | Miyauchi et al. | |
| 2009/0263844 A1 | 10/2009 | Itoh | |
| 2009/0280514 A1 | 11/2009 | Katayama et al. | |
| 2009/0317846 A1 | 12/2009 | Itoh | |
| 2010/0035288 A1 | 2/2010 | Itoh | |
| 2010/0041080 A1 | 2/2010 | Aratake et al. | |

FOREIGN PATENT DOCUMENTS

| | | |
|---|---|---|
| WO | WO 2004/053500 A1 | 6/2004 |
| WO | WO 2006/085654 A1 | 8/2006 |
| WO | WO 2006/118199 A1 | 11/2006 |
| WO | WO 2007/026829 A1 | 3/2007 |
| WO | WO 2007/126099 A1 | 8/2007 |
| WO | WO 2008/105486 A1 | 4/2008 |
| WO | WO 2008/050636 A1 | 5/2008 |

OTHER PUBLICATIONS

International Search Report PCT/JP2008/068489 dated Dec. 9, 2008.
T. Hirano et al., "A Novel and Simple Method for Quantification of Small, Dense LDL", Journal of Lipid Research vol. 44, 2003, pp. 2193-2201.
Supplementary European Search Report EP 08 83 7388 dated Feb. 25, 2011.
Yasuki Ito et al., "Development of a Homogeneous Assay for Measurement of Small Dense LDL Cholesterol", Clinical Chemistry 57:1, 57-65 (2011).

* cited by examiner

*Primary Examiner* — Suzanne M Noakes
(74) *Attorney, Agent, or Firm* — Foley & Lardner LLP

(57) ABSTRACT

A method for fractional measurement of small, dense LDL, which is adaptable for an autoanalyzer, and a reagent for measurement, are provided, making it possible to conduct rapid and convenient analysis with good sensitivity without pretreatment of a specimen. The method for quantitatively determining small, dense LDL cholesterol in a sample comprises the steps of:

(1) eliminating cholesterol in LDL other than small, dense LDL in the presence of phospholipase; and
(2) quantitatively determining cholesterol in lipoproteins remaining in step (1) above.

4 Claims, 11 Drawing Sheets

METHOD AND KIT FOR QUANTITATIVELY DETERMINING SMALL, DENSE LDL CHOLESTEROL

CROSS-REFERENCE TO RELATED APPLICATIONS

This application is a divisional of U.S. patent application Ser. No. 12/682,240, filed on Apr. 8, 2010, which is a national phase entry of PCT application No. PCT/JP2008/068489, filed on Oct. 10, 2008, which claims priority to Japanese patent application No. 2007-264908, filed on Oct. 10, 2007. The contents of these prior applications are incorporated herein by reference in their entireties.

TECHNICAL FIELD

The present invention relates to a method and a reagent for measuring cholesterol in small, dense LDL, which is important for diagnosis of arteriosclerosis.

BACKGROUND ART

Cholesterol is an important constituent of cells and is also a clinically important constituent since an excessive level of cholesterol causes transformation of macrophages into foam cells after uptake thereof by macrophages in the subendothelial space and then causes development of a primary lesion of arteriosclerosis. Low density lipoprotein (LDL) play a major role in cholesterol transport in the blood and are risk factors for arteriosclerosis. It is known that small, dense LDL, which are particularly small in particle size among LDL and higher in density compared with standard LDL, is more several fold atherogenic than normal LDL. Increase of small, dense LDL is one of the major risk factors for arteriosclerosis. It is clinically very important to perform a fractional measurement for such small, dense LDL.

Examples of conventional methods for measurement of small, dense LDL include an ultracentrifugation method, an electrophoresis method, and a method using high performance liquid chromatography. These methods are not convenient since they require expensive facilities and much time for measurement.

An example of a method for measuring small, dense LDL using an autoanalyzer is a method (see JP Patent Publication (Kokai) No. 2003-28882 A) that involves suspending or dissolving small particle LDL with the use of differences in ionic strength and then conducting measurement on the small particle LDL with the use of differences in absorbance. However, differences in absorbance are measured based on turbidity according to such method. Hence, cholesterol in small, dense LDL cannot be measured and thus specificity and accuracy are insufficient.

Also, a method (International Patent Publication WO2004/053500) that involves measuring cholesterol or triglyceride in small, dense LDL through the use of a combination of a separating agent comprising polyanions and a divalent cation and a reagent adaptable for an autoanalyzer is known. This method is capable of measuring lipid components in small, dense LDL more conveniently than an ultracentrifugation method or an electrophoresis method. Furthermore, the method is excellent in specificity and accuracy. However, the method requires pretreatment of specimens and a procedure for separating LDL into small, dense LDL and LDL other than such LDL.

DISCLOSURE OF THE INVENTION

Object to be Achieved by the Invention

An object of the present invention is to provide a method for fractional measurement of small, dense LDL, which is adaptable for an autoanalyzer, and a reagent for such measurement, both of which enable rapid and convenient analysis with good specificity without pretreatment of a specimen.

Means to Achieve the Object

As a result of concentrated studies, the present inventors have completed a novel method for measuring small, dense LDL. Specifically, when cholesterol in a sample containing various lipoproteins is measured using cholesterol esterase and cholesterol oxidase or cholesterol dehydrogenase, the reaction rate of an enzyme against LDL other than small, dense LDL increases to a greater extent than that of an enzyme against small, dense LDL because of the use of phospholipase reacting specifically with a specific substrate. Thus, cholesterol in LDL other than small, dense LDL could be eliminated and led outside of the reaction system with the use of catalase or 4 aminoantipyrine. Thereafter, an enzyme reaction was conducted using an enzyme for cholesterol measurement, so that cholesterol, particularly in small, dense LDL, among LDL could be measured. Moreover, when a specific surfactant reacting with lipoproteins other than LDL such as HDL and VLDL was added before or after the reaction to lead LDL other than small, dense LDL outside of the reaction system, the specific surfactant reacted with lipoproteins such as HDL and VLDL other than LDL, so that cholesterol in HDL or VLDL could be eliminated and led outside of the reaction system by catalase or 4 aminoantipyrine. Such reaction for elimination of LDL other than small, dense LDL and the reaction for eliminating cholesterol in HDL or VLDL through the reaction of lipoproteins such as HDL and VLDL with a specific surfactant were conducted simultaneously, so that lipoproteins other than small, dense LDL could be eliminated and led outside of the reaction system. The thus remaining small, dense LDL were reacted with an enzyme for cholesterol measurement, so that cholesterol in small, dense LDL could be successfully fractioned and measured alone. Furthermore, the types of surfactant and the concentrations of enzymes were specified, so that both the reaction for eliminating the above lipoproteins other than small, dense LDL so as to lead them outside of the reaction system and the reaction for eliminating cholesterol in HDL and VLDL so as to lead it outside of the reaction system could be successfully conducted with the same solution. Thus, the present invention was completed.

The present invention is as described below.

[1] A method for quantitatively determining small, dense LDL cholesterol in a sample, comprising the steps of:
(1) eliminating cholesterol in LDL other than small, dense LDL in the presence of phospholipase, and then
(2) quantitatively determining cholesterol in small, dense LDL.

[2] The method for quantitatively determining small, dense LDL cholesterol according to [1], wherein phospholipase to be used in step (1) has high reactivity with at least sphingomyelin and/or phosphatidylinositol, which is a phospholipid existing in lipoproteins.

[3] The method for quantitatively determining small, dense LDL cholesterol according to [1] or [2], wherein the concentration of phospholipase to be used in step (1) ranges from 0.1 U/mL to 100 U/mL.

[4] The method for quantitatively determining small, dense LDL cholesterol according to any one of [1] to [3], wherein an enzyme for cholesterol measurement is added in the presence of a surfactant that acts on at least small, dense LDL in step (2).

[5] The method for quantitatively determining small, dense LDL cholesterol according to [4], wherein the surfactant that acts on at least small, dense LDL, which is used in step (2), is a surfactant that acts on all lipoproteins.

[6] The method for quantitatively determining small, dense LDL cholesterol according to [4] or [5], wherein the surfactant that acts on at least small, dense LDL, which is used in step (2), is a polyoxyethylene-polyoxypropylene copolymer or a derivative thereof, or a polyoxyethylene derivative with HLB of 11 or more and less than 14.

[7] The method for quantitatively determining small, dense LDL cholesterol according to any one of [1] to [6], further comprising step (a) of eliminating cholesterol in lipoproteins other than LDL in a sample in the presence of cholesterol esterase, which is carried out before step (2), but simultaneously with, before, or after step (1).

[8] The method for quantitatively determining small, dense LDL cholesterol according to [7], wherein the concentration of cholesterol esterase to be used in step (a) ranges from 0.01 U/mL to 10 U/mL.

[9] The method for quantitatively determining small, dense LDL cholesterol according to [7] or [8], wherein a surfactant that acts on lipoproteins other than LDL is further added in step (a).

[10] The method for quantitatively determining small, dense LDL cholesterol according to [9], wherein the concentration of the surfactant to be used in step (a) ranges from 0.05% to 1.0%.

[11] The method for quantitatively determining small, dense LDL cholesterol according to any one of [7] to [10], wherein cholesterol oxidase and catalase are further added in step (a).

[12] The method for quantitatively determining small, dense LDL cholesterol according to any one of [7] to [10], wherein 4 aminoantipyrine is further added in step (a).

[13] The method for quantitatively determining small, dense LDL cholesterol according to any one of [7] to [12], wherein the reaction in step (a) and the reaction in step (1) are conducted simultaneously in the same solution.

[14] The method for quantitatively determining small, dense LDL cholesterol according to any one of [7] to [13], wherein the surfactant to be used in step (a) is a nonionic surfactant selected from the group consisting of a polyoxyethylene derivative, polyoxyethylene alkyl ether, polyoxyethylene alkyl phenyl ether, and polyoxyethylene alkyl amine, an anionic surfactant selected from the group consisting of polyoxyethylene alkyl ether sulfate, alkyl sulfate, amide ether sulfate, alkyl taurate, and a phosphate-type surfactant, a cationic surfactant selected from the group consisting of an alkyl methyl ammonium salt, a quaternary ammonium salt, and a mono-linear alkyl type surfactant, or an amphoteric surfactant selected from the group consisting of lauryl betaine, dimethyl alkyl betaine, an imidazoline type surfactant, and sodium alkyldiaminoethyl glycine.

[15] A kit for quantitatively determining small, dense LDL cholesterol, containing at least the following two types of reagent composition:
(i) a reagent composition for eliminating cholesterol in LDL other than small, dense LDL in a sample, containing at least phospholipase that reacts with LDL other than small, dense LDL;

(ii) a reagent composition for measurement of small, dense LDL, containing: a surfactant that is a polyoxyethylene-polyoxypropylene copolymer that reacts with only small, dense LDL or a derivative thereof; or
a surfactant that is a polyoxyethylene derivative with HLB of 11 or more and less than 14;
4 aminoantipyrine; and
peroxidase.

[16] The kit for quantitatively determining small, dense LDL cholesterol according to [15] containing at least 3 reagent compositions, which further contains (iii) a reagent composition for eliminating cholesterol in lipoproteins other than LDL containing: a nonionic surfactant selected from the group consisting of at least polyoxyethylene alkyl ether, polyoxyethylene alkyl phenyl ether, and polyoxyethylene alkyl amine; an anionic surfactant selected from the group consisting of polyoxyethylene alkylether sulfate, alkyl sulfate, amide ether sulfate, alkyl taurate, and a phosphate-type surfactant; a cationic surfactant selected from the group consisting of an alkyl methyl ammonium salt, a quaternary ammonium salt, and a mono-linear alkyl type surfactant; or an amphoteric surfactant selected from the group consisting of lauryl betaine, dimethyl alkyl betaine, an imidazoline type surfactant, and sodium alkyldiaminoethyl glycine.

[17] The kit for quantitatively determining small, dense LDL cholesterol according to [15], wherein the reagent composition (i) further contains: a nonionic surfactant selected from the group consisting of at least polyoxyethylene alkyl ether, polyoxyethylene alkyl phenyl ether, and polyoxyethylene alkyl amine; an anionic surfactant selected from the group consisting of polyoxyethylene alkylether sulfate, alkyl sulfate, amide ether sulfate, alkyl taurate, and a phosphate-type surfactant; a cationic surfactant selected from the group consisting of an alkyl methyl ammonium salt, a quaternary ammonium salt, and a mono-linear alkyl type surfactant; or an amphoteric surfactant selected from the group consisting of lauryl betaine, dimethyl alkyl betaine, an imidazoline type surfactant, and sodium alkyldiaminoethyl glycine, whereby
cholesterol in lipoproteins other than small, dense LDL in a sample is eliminated by the reagent composition (i).

[18] The kit for quantitatively determining small, dense LDL cholesterol according to any one of [15] to [17], wherein the phospholipase has high reactivity with at least sphingomyelin and/or phosphatidylinositol among phospholipids existing in lipoproteins.

Effect of the Invention

Through addition of a reagent containing a specific surfactant of the present invention; that is, phospholipase to a sample containing lipoproteins, small, dense LDL among lipoproteins can be directly and selectively measured without carrying out separation using a filter or centrifugation.

The description includes part or all of the contents as disclosed in the description and/or drawings of Japanese Patent Application No. 2007-264908, which is a priority document of the present application.

BRIEF DESCRIPTION OF THE DRAWINGS

FIG. 2 shows the correlation between:

the method of the present invention, which comprises 3 steps wherein the first step is a step of eliminating cholesterol in lipoproteins other than LDL so as to lead the cholesterol outside of the reaction system and uses phospholipase C as phospholipase; and a method using a sd LDL-C "SEIKEN" reagent for measurement of small, dense LDL cholesterol.

Figure 3:
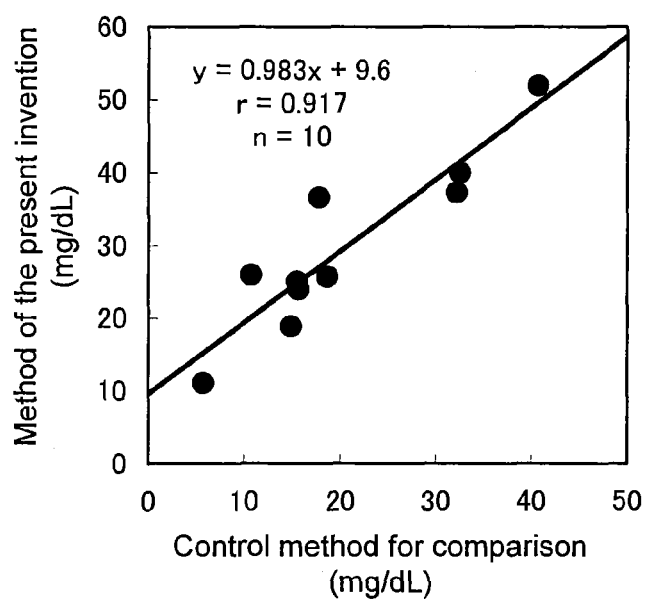

FIG. 3 shows the correlation between:

the method of the present invention, which comprises 3 steps wherein the first step is a step of eliminating cholesterol in lipoproteins other than LDL so as to lead the cholesterol outside of the reaction system and uses phospholipase D as phospholipase; and a method using a sd LDL-C "SEIKEN" reagent for measurement of small, dense LDL cholesterol.

Figure 4:
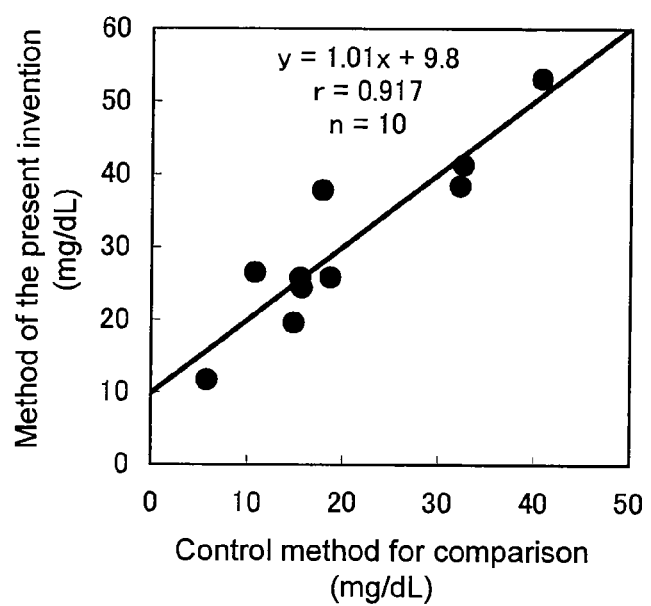

FIG. 4 shows the correlation between:

the method of the present invention, which comprises 3 steps wherein the first step is a step of eliminating cholesterol in lipoproteins other than LDL so as to lead the cholesterol outside of the reaction system and uses lysophospholipase as phospholipase; and a method using a sd LDL-C "SEIKEN" reagent for measurement of small, dense LDL cholesterol.

Figure 5:
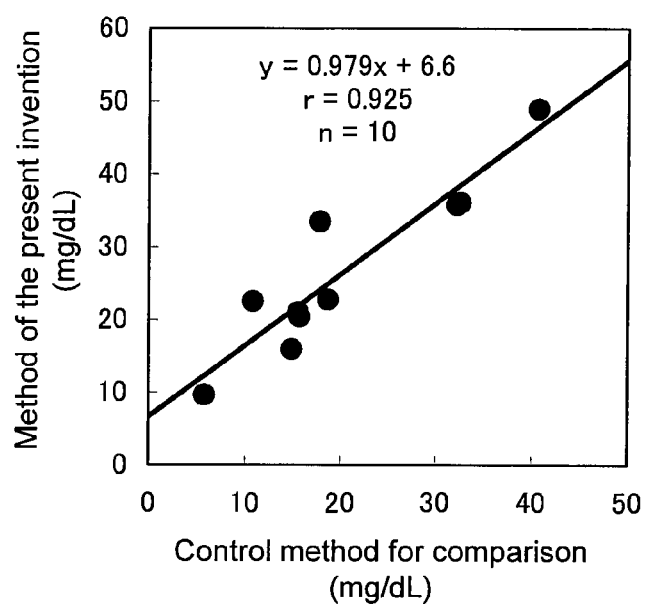

FIG. 5 shows the correlation between:

the method of the present invention, which comprises 3 steps and uses phospholipase specific to glycerophospholipid as phospholipase; and a method using a sd LDL-C "SEIKEN" reagent for measurement of small, dense LDL cholesterol.

Figure 6:
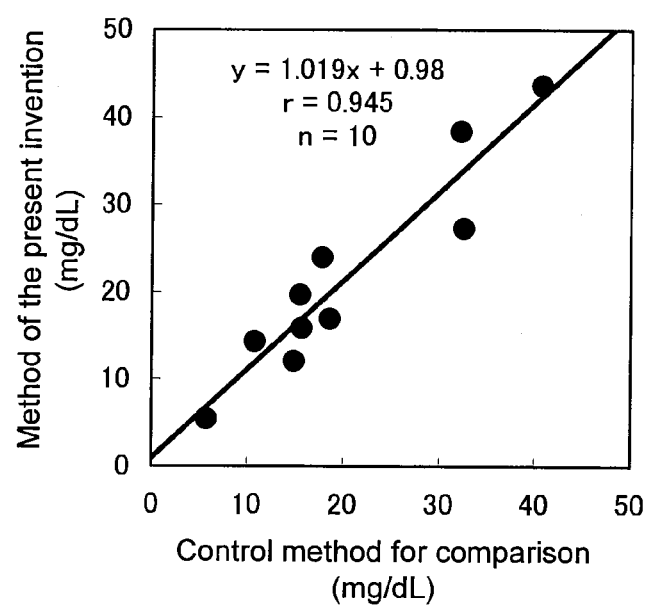

FIG. 6 shows the correlation between:

the method of the present invention, which comprises 3 steps wherein the first step is a step of eliminating cholesterol in lipoproteins other than LDL so as to lead the cholesterol outside of the reaction system and uses sphingomyelinase as phospholipase; and a method using a sd LDL-C "SEIKEN" reagent for measurement of small, dense LDL cholesterol.

Figure 7:
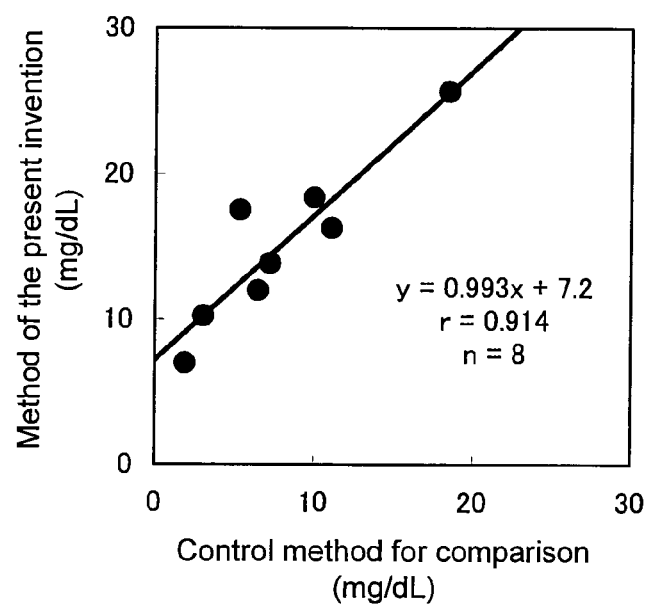

FIG. 7 shows the correlation between:

the method of the present invention, which comprises 3 steps wherein the first step is a step of eliminating cholesterol in LDL (L LDL) other than small, dense LDL among LDL so as to lead the cholesterol outside of the reaction system and uses sphingomyelinase as phospholipase; and a method using a sd LDL-C "SEIKEN" reagent for measurement of small, dense LDL cholesterol.

Figure 8:
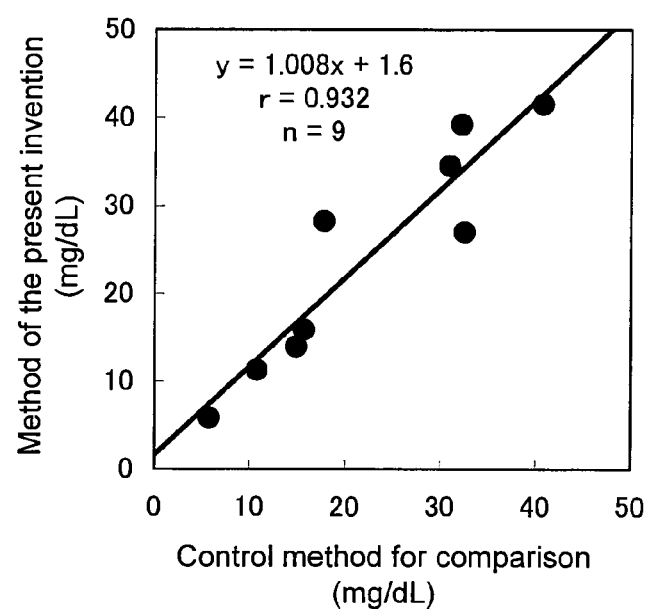

FIG. 8 shows the correlation between:

the method of the present invention, which comprises 2 steps, uses sphingomyelinase as phospholipase, and uses EMULGEN B-66 and EMULGEN A-90 as surfactants; and a method using a sd LDL-C "SEIKEN" reagent for measurement of small, dense LDL cholesterol.

Figure 9:
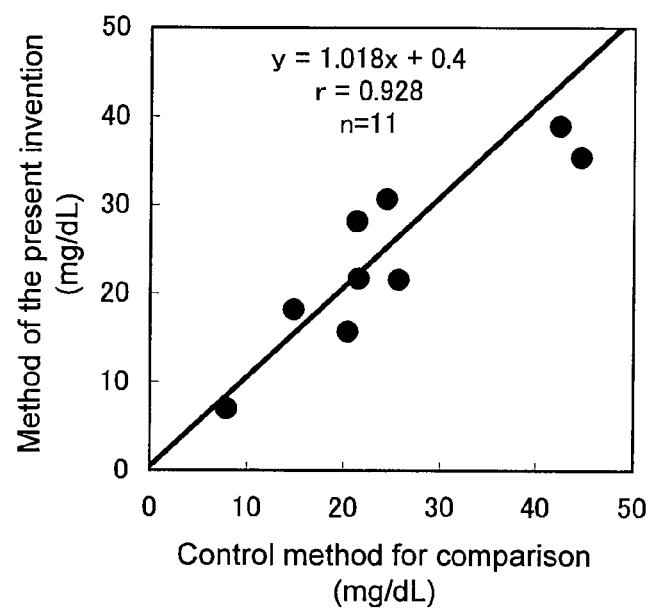

FIG. 9 shows the correlation between:

the method of the present invention, which comprises 3 steps, uses sphingomyelinase as phospholipase, and uses EMULGEN B-66 as a surfactant; and a method using a sd LDL-C "SEIKEN" reagent for measurement of small, dense LDL cholesterol.

Figure 10:
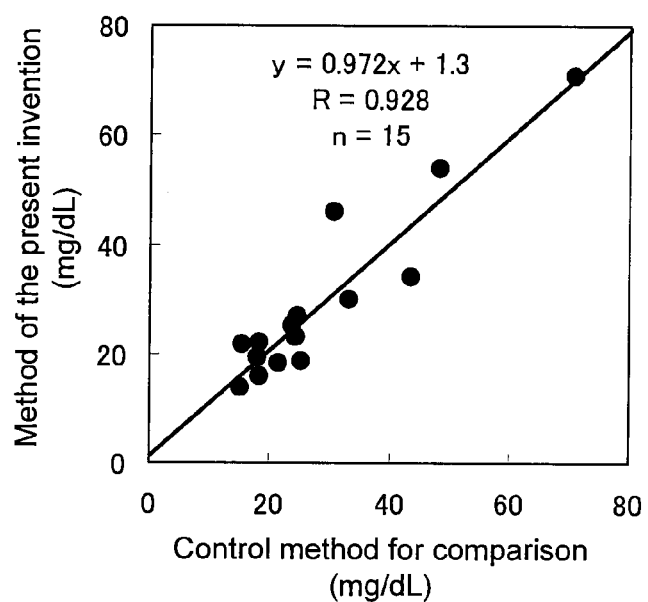

FIG. 10 shows the correlation between:

the method of the present invention, which comprises 2 steps, uses sphingomyelinase as phospholipase, and uses EMULGEN A-90 as a surfactant; and a method using a sd LDL-C "SEIKEN" reagent for measurement of small, dense LDL cholesterol.

Figure 11:
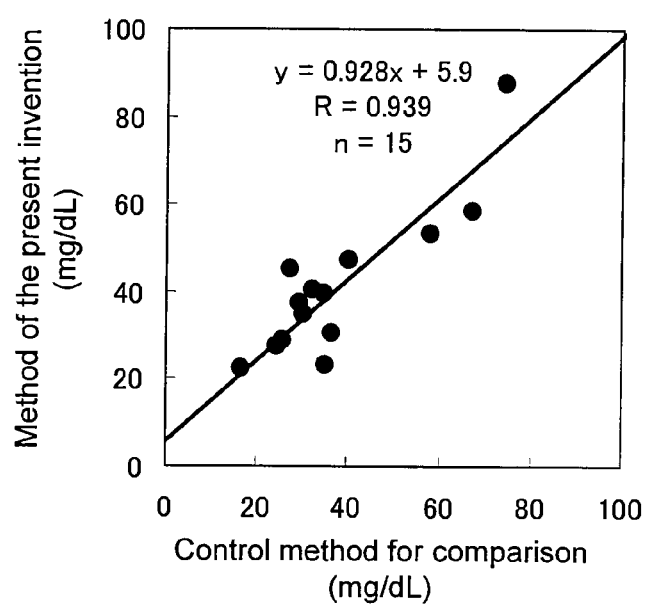

FIG. 11 shows the correlation between:

the method of the present invention, which comprises 2 steps, uses sphingomyelinase as phospholipase, and uses no surfactant; and a method using a sd LDL-C "SEIKEN" reagent for measurement of small, dense LDL cholesterol.

BEST MODE FOR CARRYING OUT THE INVENTION

The present invention will be explained in detail as follows.

Lipoproteins can be fractionated roughly into VLDL, LDL, and HDL. LDL is further fractionated into small, dense LDL and other sub-fractions. Small, dense LDL is also referred to as small particle LDL, SLDL (small LDL), dense LDL, or sd LDL. LDL other than them may also be referred to as L LDL (large LDL) or light LDL. These fractions may be distinguished from sub-fractions based on particle size or density. The particle size (or particle diameter) of VLDL ranges from 30 nm to 80 nm (30 nm to 75 nm), that of LDL ranges from 22 nm to 28 nm (19 nm to 30 nm), and that of HDL ranges from 7 nm to 10 nm, although such figures may vary depending on researchers. The density of VLDL is 1.006 (g/l) or less, that of LDL ranges from 1.019 to 1.063 (g/l), and that of HDL ranges from 1.063 to 1.21 (g/l). The diameters of LDL particles can be measured by gradient gel electrophoresis (GGE) (JAMA, 260, p. 1917-21, 1988) or NMR (HANDBOOK OF LIPOPROTEIN TESTING $2^{nd}$ Edition, Edited by Nader Rifai et al. p. 609-623, AACC PRESS: The Fats of Life Summer 2002, LVDD 15 YEAR ANNIVERSARY ISSUE, Volume AVI No. 3, p. 15-16). Density can be determined based on analyses by ultracentrifugation (Atherosclerosis, 106, p. 241-253, 1994: Atherosclerosis, 83, p. 59, 1990).

Small, dense LDL to be measured by the method of the present invention are generally sub-fractions with diameters ranging from approximately 22.0 nm to approximately 25.5 nm and density ranging from 1.040 to 1.063 (g/l), among LDL fractions. The reason why LDL is sub-fractionated based on particle size is that small LDL among LDL needs to be fractionally measured because such LDL with small particle sizes have a high tendency of inducing arteriosclerosis and have particularly higher malignancy than that of other LDL. The distributions of diameter and density of LDL are continuous. Thus, it is impossible to clearly determine that an LDL with a density that is at the aforementioned level or higher results in a particularly high degree of malignancy. Thus, the density ranging from 1.040 to 1.063 (g/l) do not constitute an established characteristic of small, dense LDL, but are values obtained by dividing the density range between 1.019 and 1.063 (g/l) at the center point, a process that has been widely used and well established. For example, in another report, small, dense LDL is fractionated in the range between 1.044 and 1.060 (g/l) (Atherosclerosis: 106 241-253 1994). There are some differences among researchers on how to set the range of density for small, dense LDL. In all cases, the presence of small, dense LDL is associated with clinical malignancy when fractionation is performed using such density range.

In the present invention, the term "small, dense LDL" refers to LDL that has a high density among LDL and clinically has a higher tendency of inducing arteriosclerosis than other LDL. Preferably, small, dense LDL has a density higher than the center point within the entire density range of LDL. More preferably, small, dense LDL has a density within the range between 1.040 and 1.063 (g/L). Also, the term "lipoproteins other than LDL" refers to VLDL and HDL. This term may further refer to chylomicron, IDL (intermediate density lipoprotein) and HDL (very high density lipoprotein).

The method of the present invention comprises the steps of:
eliminating cholesterol in LDL (L LDL) other than small, dense LDL among LDL, so as to lead the cholesterol outside of the reaction system;
eliminating cholesterol in lipoproteins other than LDL, so as to lead the cholesterol outside of the reaction system; and
measuring small, dense LDL.

For the above step of eliminating cholesterol in LDL (L LDL) other than small, dense LDL from among LDL so as to lead the cholesterol outside of the reaction system and the above step of eliminating cholesterol in lipoproteins other than LDL so as to lead the cholesterol outside of the reaction system, appropriate techniques can also be employed herein to lead such cholesterol outside of the reaction system, instead of eliminating it in LDL (L LDL) other than small, dense LDL or in lipoproteins other than LDL. Specifically, cholesterol contained in HDL, VLDL, L LDL, or the like can be led outside of the reaction system using a known technique involving aggregation of such cholesterol contained in HDL, VLDL, L LDL, or the like or inhibiting it from reacting in the subsequent steps, so as not to affect quantitative determination of small, dense LDL cholesterol, for example.

In the step of leading cholesterol in LDL (L LDL) other than small, dense LDL from among LDL outside of the reaction system, another reaction is thought to take place in addition to the reaction by which cholesterol in LDL (L LDL) other than small, dense LDL in this step is led outside of the reaction system. Such "another reaction" is acceptable in the method of the present invention, as long as the reaction does not affect a purpose of the present invention; that is, fractional measurement of small, dense LDL. An example of such "another reaction" is a reaction by which cholesterol in lipoproteins other than LDL is led outside of the reaction system. This reaction is acceptable since it does not generally affect fractional measurement of small, dense LDL.

The method of the present invention is generally carried out within an autoanalyzer.

In the step of the method of the present invention of eliminating cholesterol in LDL (Large LDL; L LDL) other than small, dense LDL, so as to lead the cholesterol outside of the reaction system, phospholipase is used. The rate of reaction of phospholipase with L LDL is higher than that of the same with small, dense LDL. Hence, phospholipase selectively increases the enzyme reaction rate when L LDL (among LDL) is used as a substrate. Phospholipase is a generic name of enzymes reacting with phospholipids. Examples of phospholipase include phospholipase A2, phospholipase C, and phospholipase D. Any types of phospholipase can be used in the present invention. Moreover, among phospholipids, phospholipase (sphingomyelinase) having high reactivity (sphingomyelinase activity) to sphingomyelin, phospholipase having high reactivity to phosphatidylinositol, and the like can be appropriately used in the present invention. The above phospholipase having high reactivity (sphingomyelinase activity) to sphingomyelin, phospholipase having high reactivity to phosphatidylinositol, and the like may also have activity to phosphatidylcholine or the like that is another phospholipid. The concentration of the above phospholipase in a reagent preferably ranges from 0.1 U/mL to 100 U/mL and more preferably ranges from 0.2 U/mL to 20 U/mL. The concentration of the same in a reaction solution upon reaction preferably ranges from 0.05 U/mL to 100 U/mL and more preferably ranges from 0.1 U/mL to 20 U/mL. Also, in addition to phospholipase having high sphingomyelinase activity and/or phospholipase having high reactivity to phosphatidylinositol, other types of phospholipase such as phospholipase A2, phospholipase D, and lysophospholipase can also be used. As the above phospholipase, phospholipase having high specificity to sphingomyelin or phospholipase having high specificity to phosphatidylinositol can be appropriately used. Phospholipase from a bacterium, yeast, or human placenta can be preferably used. Preferable specific examples of phospholipase include, but are not limited to, PLA2, PLC, PLD, LYPL, PLDP, SPC, and PI-PLC (Asahi Kasei Corporation), Sphingomyelinase from *Bacillus cereus*, Sphingomyelinase from *Staphylococcus aureus*, phospholipase C, and phosphatidylinositol-specific from *Bacillus cereus* (SIGMA).

A surfactant may be used or not used in the step of eliminating cholesterol in L LDL. The use of a preferable surfactant enables accelerated elimination of cholesterol in L LDL. When a surfactant is used, a surfactant that is the same as that used in the step of eliminating cholesterol in lipoproteins such as VLDL and HDL other than the following LDL can be preferably used. Also, a suitable surfactant differing from such example may also be added.

When the step of eliminating cholesterol in lipoproteins other than LDL is carried out before the step of eliminating cholesterol in L LDL, each component in the step of eliminating cholesterol in lipoproteins other than LDL remains intact when it is subjected to the subsequent step of eliminating cholesterol in L LDL. Hence, surfactant(s) used for eliminating cholesterol in lipoproteins other than LDL can also be used in the step of eliminating cholesterol in L LDL.

In the above step of eliminating cholesterol in L LDL, cholesterol esterase acts on L LDL in the presence of phospholipase, the thus generated cholesterol is reacted and eliminated in the presence of an enzyme reacting with cholesterol, such as cholesterol oxidase or cholesterol dehydrogenase. Following this, cholesterol in L LDL is led outside of the reaction system. When a surfactant is used in the step of eliminating cholesterol in L LDL, cholesterol esterase and the surfactant act on L LDL in the presence of phospholipase, the thus generated cholesterol is reacted and eliminated in the presence of an enzyme reacting with cholesterol, such as cholesterol oxidase or cholesterol dehydrogenase, and thus cholesterol in L LDL is led outside of the reaction system. Here, the phrase "surfactant acts on (reacts with)" refers to a situation in which a surfactant binds to lipoproteins to alter or degrade them, for example, so that cholesterol in lipoproteins is liberated. For example, when "a surfactant acts on (reacts with) lipoproteins other than LDL," the surfactant is not required to never act on LDL, but may act mainly on lipoproteins other than LDL. For example, a surfactant that acts on lipoproteins other than small, dense LDL has fewer effects on small, dense LDL than on lipoproteins other than small, dense LDL. The term "elimination" means to degrade a substance in a test sample so as to prevent the degraded product from being detected in the subsequent step. That is, the phrase "eliminating cholesterol in lipoproteins in L LDL" means to degrade L LDL in a sample and then to prevent the degraded product; that is, cholesterol in L LDL from being detected in the subsequent step. Examples of a method for elimination include, but are not limited to, a method that involves degrading hydrogen peroxide (generated by causing cholesterol esterase or cholesterol oxidase to act) into water and oxygen using catalase and a method that involves causing a hydrogen donor to react with hydrogen peroxide using peroxidase, so as to perform conversion into colorless quinone.

In the present invention, the phrase "led (or . . . leading . . . ) the outside of the reaction system" refers to a system in which cholesterol contained in HDL, VLDL, L LDL, or the like is eliminated, aggregated, or inhibited to avoid its reaction in the subsequent steps, for example, in order to prevent such cholesterol contained in HDL, VLDL, L LDL, or the like from affecting quantitative determination of small, dense LDL cholesterol.

In the present invention, a step of eliminating cholesterol in lipoproteins such as VLDL and HDL other than LDL can also be carried out in addition to the above step of eliminating cholesterol in L LDL in the presence of phospholipase. The step of eliminating cholesterol in lipoproteins such as VLDL and HDL other than LDL may be carried out before, after, or simultaneously with the step of eliminating cholesterol in L LDL.

In the step of eliminating cholesterol in lipoproteins such as VLDL and HDL other than LDL, cholesterol in VLDL and HDL is eliminated in the presence of a surfactant that acts on lipoproteins such as VLDL and HDL other than LDL but does not react with LDL. An example of such surfactant that acts on and reacts with VLDL, HDL, and the like other than LDL is a polyoxyethylene derivative with HLB of 13 or more and 15 or less. The concentration of such surfactant in a reagent preferably ranges from 0.3% (w/v) to 5% (w/v) and more preferably ranges from 0.5% (w/v) to 3% (w/v). The concentration thereof in a reaction solution upon reaction preferably ranges from 0.15% to 5% and more preferably ranges from 0.25% (w/v) to 3% (w/v). Examples of such derivative include higher alcohol condensates, higher fatty acid condensates, higher fatty acid amide condensates, higher alkylamine condensates, higher alkyl mercaptan condensates, and alkylphenol condensates. Preferable specific examples of a polyoxyethylene derivative with HLB of 13 or more and 15 or less include, but are not limited to, compounds with HLB of 13 or more and 15 or less, such as polyoxyethylene laurylether, polyoxyethylene cetylether, polyoxyethylene oleylether, polyoxyethylene higher alcohol ether, and polyoxyethylene alkylphenyl ether. Specific examples of the above surfactant include EMULGEN B-66 (polyoxyethylene derivative), and EMULGEN A-90 (polyoxyethylene distyrenated phenylether).

When a surfactant that does not react with small, dense LDL, but reacts with only L LDL is used in the step of eliminating cholesterol in L LDL, as such surfactant with HLB of 13 or more and 15 or less, a nonionic surfactant selected from the group consisting of a polyoxyethylene derivative, polyoxyethylene alkyl ether, and polyoxyethylene alkyl amine, an anionic surfactant selected from the group consisting of polyoxyethylene alkylether sulfate, alkyl sulfate, amide ether sulfate, alkyl taurate, and a phosphate-type surfactant, a cationic surfactant selected from the group consisting of an alkyl methyl ammonium salt, a quaternary ammonium salt, and a mono-linear alkyl type surfactant, or an amphoteric surfactant selected from the group consisting of lauryl betaine, dimethyl alkyl betaine, an imidazoline type surfactant, and sodium alkyldiaminoethyl glycine may be added. Specific examples of such nonionic surfactant include EMULGEN B-66, EMULGEN A-90, EMULGEN 120, and EMULGEN 920 (Kao Corporation), NONION HS-220, NONION HS-215, NONION K-230, NONION NS-220, NONION NS-230, NYMEEN F-215, NYMEEN L-207, and ADEKA TOL LB-1520 (ADEKA Corporation). Specific examples of such anionic surfactant include EMAL 20CM, EMAL 20T, EMAL E27C, and LEVENOL WX (Kao Corporation), SUNAMIDE CF-3, SUNAMIDE CF-10, DIAPON K, DIAPON F, DIAPON K-SF, PERSOFT EF, PERSOFT EFT, PERSOFT EL, PERSOFT EP, PERSOFT EK, PERSOFT SL, POLYSTAR OMP (NOF Corporation), ADEKA COL PS-440E, and TRAX K-40 (ADEKA Corporation). Specific examples of such cationic surfactant include QUARTAMIN 24P (Kao Corporation), and ADEKA MINE 4 MAC-30 (ADEKA Corporation). Specific examples of such amphoteric surfactant include AMPHITOL 24B (Kao Corporation), NISSAN ANON LG, NISSAN ANON BDF-R, NISSAN ANON BF, NISSAN ANON BL, NISSAN ANON BL-SF, and NISSAN ANON GLM-R-LV. The concentration of the above surfactant in a reagent preferably ranges from approximately 0.01% (w/v) to 1.0% (w/v) and further preferably ranges from approximately 0.10% (w/v) to 0.50% (w/v). The concentration of such surfactant in a reaction solution upon reaction preferably ranges from approximately 0.005% (w/v) to 1.0% (w/v) and more preferably ranges from approximately 0.05% (w/v) to 0.50% (w/v).

Cholesterol esterase and cholesterol oxidase are caused to act in the presence of the above surfactant to generate hydrogen peroxide from cholesterol and then the thus generated hydrogen peroxide is eliminated. Examples of a method for eliminating hydrogen peroxide include, but are not limited to, a method that involves causing catalase to act so as to degrade hydrogen peroxide into water and oxygen and a method that involves causing a phenol or aniline hydrogen donor compound to react with hydrogen peroxide using peroxidase, so as to perform conversion into colorless quinone. The concentration of cholesterol esterase in a reaction solution preferably ranges from approximately 0.010 U/mL to 10 U/mL. Also, cholesterol oxidase from a bacterium or from yeast can be used. The concentration of such cholesterol oxidase in a reaction solution preferably ranges from approximately 0.1 U/mL to 0.7 U/mL. Moreover, the concentration of catalase in a reaction solution preferably ranges from approximately 40 U/mL to 500 U/mL. Also, the concentration of peroxidase in a reaction solution when hydrogen peroxide is converted into colorless quinine preferably ranges from 0.4 U/mL to 1.0 U/mL and the concentration of such phenol or aniline hydrogen donor compound in a reaction solution preferably ranges from 0.4 mmol/L to 0.8 mmol/L.

The above components involved in elimination, such as cholesterol oxidase, catalase, peroxidase, and the phenol or aniline hydrogen donor compound, may be used in either the step of eliminating L LDL or the step of eliminating HDL, VLDL, and the like other than LDL or in both steps.

The amount of a reagent to be used in the step of eliminating cholesterol in L LDL and the amount of a reagent to be used in the step of eliminating cholesterol in lipoproteins other than LDL may be determined in view of the concentration range of each component. For example, suppose that the concentration of a surfactant to be used in the step of eliminating cholesterol in lipoproteins other than LDL is 3 g/L, no surfactant is added in the step of eliminating cholesterol in L LDL, and the fluid volume ratio of a reagent to be used in the step of eliminating cholesterol in lipoproteins other than LDL to a reagent to be used in the step of eliminating cholesterol in L LDL is 1:1. When the amount of a sample is small, the concentration of the surfactant in the step is approximately 1.5 g/L. In this manner, the composition of a reagent and the amount of a reagent to be added can be determined in view of the concentration of a reagent required upon reaction.

Through the step of eliminating cholesterol in L LDL and the step of eliminating cholesterol in lipoproteins other than LDL, cholesterol in lipoproteins, which has acted on and reacted with the above surfactant and cholesterol esterase, is caused to react with an enzyme reacting with cholesterol, such as cholesterol oxidase or cholesterol dehydrogenase, so as to lead it outside of the reaction system. Cholesterol in lipoproteins such as VLDL and HDL other than LDL and L LDL is led outside of the reaction system through such reaction, so that in the subsequent step, small, dense LDL alone remain as lipoprotein in the reaction solution. In the present invention, such procedures of eliminating lipoproteins other than small, dense LDL and then leading them outside of the reaction system, so as to prevent the detection of cholesterol in lipoproteins other than small, dense LDL in the subsequent step may also be described as "differentiating small, dense LDL from lipoproteins other than small, dense LDL."

Also, through adjustment of the concentration of cholesterol esterase in the presence of the above surfactant, the type of a lipoprotein reacting with cholesterol esterase can be changed, making it possible to selectively eliminate lipoproteins other than small, dense LDL. As the concentration of cholesterol esterase upon reaction increases, first the reactivity of L LDL, in particular (among LDL), with an enzyme, increases, so that they are led outside of the reaction system. However, within a range in which the concentration is not so high, the reactivity of small, dense LDL with an enzyme shows no increase. Furthermore, when the concentration of cholesterol esterase increases, the reactivity of small, dense LDL with an enzyme increases. As such, when cholesterol esterase is added at a concentration within a range in which the reactivity between L LDL and an enzyme is high and the reactivity between small, dense LDL and an enzyme is low, small, dense LDL can be selectively measured. Accordingly, small, dense LDL can be more selectively measured by adjusting the concentration of cholesterol esterase to within a specific range. The concentration of cholesterol esterase in a reaction solution for the step of eliminating cholesterol in L LDL and leading it outside of the reaction system or the same for the step of eliminating cholesterol in lipoproteins other than LDL and leading it outside of the reaction system preferably ranges from 0.1 U/mL to 3.0 U/mL, further preferably ranges from 0.3 U/mL to 2.5 U/mL, and particularly preferably ranges from 0.6 U/mL to 2.0 U/mL. Cholesterol esterase to be used in the present invention is not particularly limited, as long as it is an enzyme that hydrolyzes cholesterol ester. Cholesterol esterase from an animal or a microorganism can be used.

Cholesterol dehydrogenase to be used herein is not particularly limited, as long as it is an enzyme capable of oxidizing cholesterol so as to reduce the oxidized coenzyme. Animal- or microorganism-derived cholesterol dehydrogenase can be used. The concentration of cholesterol dehydrogenase in a reaction solution preferably ranges from 0.01 U/mL to 200 U/mL and particularly preferably ranges from 0.1 U/mL to 100 U/mL.

Lipoproteinase can also be added arbitrarily to a reaction solution for the step of eliminating cholesterol in L LDL and/or the step of eliminating cholesterol in lipoproteins other than LDL in order to adjust the effects on various lipoproteins. As such lipoproteinase, lipoprotein lipase can be used. Lipoprotein lipase to be used herein is not particularly limited, as long as it is an enzyme capable of degrading lipoproteins. Animal- or microorganism-derived lipoprotein lipase can be used. The concentration of such lipoprotein lipase in a reaction solution preferably ranges from 0.01 U/mL to 10 U/mL, further preferably ranges from 0.01 U/mL to 5 U/mL, and particularly preferably ranges from 0.01 U/mL to 1 U/mL.

The step of eliminating cholesterol in L LDL and the step of eliminating cholesterol in lipoproteins other than LDL according to the present invention can be simultaneously carried out within the same reagent. In this case, the concentration of cholesterol esterase in a reaction solution preferably ranges from 0.5 U/mL to 2.0 U/mL. As a surfactant to be used herein, a surfactant to be used in the step of eliminating cholesterol in L LDL and/or the step of eliminating cholesterol in lipoproteins other than LDL can be used intact. The concentration of such surfactant in a reaction solution preferably ranges from 0.05% (w/v) to 0.3% (w/v). Also, the concentration of phospholipase in a reaction solution preferably ranges from 0.1 U/mL to 30 U/mL.

In the present invention, cholesterol in small, dense LDL that has remained unreacted in both the step of eliminating cholesterol in L LDL and the step of eliminating cholesterol in lipoproteins other than LDL is quantitatively determined in the subsequent step. A conventionally employed method for quantitatively determining LDL can be used in the quantitative determination step. Examples of such method include a method that involves adding an LDL coagulant and then quantitatively determining the content of the thus formed LDL specific aggregates by turbidimetric determination, a method that involves using an antigen-antibody reaction with an LDL specific antibody, and a method that involves quantitatively determining degraded products using enzymes. Of these methods, a preferable method involves quantitatively determining degraded products using an enzyme. Specifically, the method involves adding an enzyme for cholesterol measurement, such as cholesterol esterase, cholesterol oxidase, or cholesterol dehydrogenase, liberating and degrading cholesterol in small, dense LDL, and then quantitatively determining the reaction products. Upon the quantitative determination step, a surfactant that acts on at least small, dense LDL is used for quantitative determination of cholesterol in small, dense LDL. Such surfactant that acts on at least small, dense LDL may be a surfactant that acts on only small, dense LDL, a surfactant that acts also on other lipoproteins in addition to small, dense LDL, or a surfactant that acts on all lipoproteins.

As a surfactant that acts on only small, dense LDL, a polyoxyethylene-polyoxypropylene copolymer or a derivative thereof can be appropriately used. Examples of the polyoxyethylene-polyoxypropylene copolymer or a derivative thereof include Pluronic (trademark)-based surfactants (e.g., BASF and ADEKA Corporation) such as Pluronic 17R-4, Pluronic L-64, Pluronic PE3100, Pluronic P-85, Pluronic F-88, Pluronic P-103, and Pluronic F-127.

As a surfactant that acts on all lipoproteins, any commercially available surfactant can be used as long as it is used in reagents or the like for total cholesterol measurement. A preferred example of such surfactant is a polyoxyethylene derivative with HLB of 11 or more and less than 14 and preferably with HLB of 12 or more and less than 14. Specific examples of such surfactant include polyoxyethylenenonylphenyl ether (EMULGEN 909 (Kao Corporation)) and polyoxyethylene alkyl ether (EMULGEN 707 (Kao Corporation), and EMULGEN 709 (Kao Corporation)).

The concentration of a surfactant in a reaction solution to be used in the step of quantitatively determining small, dense LDL preferably ranges from approximately 0.01% (w/v) to 10% (w/v) and further preferably ranges from approximately 0.1% (w/v) to 5% (w/v).

When cholesterol esterase and cholesterol oxidase are used as enzymes (reacting with cholesterol) for cholesterol measurement in the step of quantitatively determining small, dense LDL, hydrogen peroxide is generated by the enzyme reaction. A dye (colored quinone) is formed from the thus generated hydrogen peroxide by a coupling reaction with a hydrogen donor and a hydrogen receptor in the presence of peroxidase. Cholesterol in small, dense LDL can be quantitatively determined through measurement of the dye at a wavelength between 400 nm and 700 nm.

A hydrogen donor that is preferably used in the quantitative determination step is an aniline derivative. Examples of such aniline derivative include N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(3-sulfopropyl)-3-methylaniline (TOPS), N-(2-hydroxy-3-sulfopropyl)-3,5-dimethoxyaniline (HDAOS), N-(3-sulfopropyl)aniline (HALPS), and N-(3-sulfopropyl)-3-methoxy-5-aniline (HMMPS). The final concentration of such hydrogen donor to be used in a reaction solution preferably ranges from 0.1 mmol/L to 1.5 mmol/L.

As a hydrogen receptor, 4-aminoantipyrine, methylbenzothiazolonhydrazone, or the like can be used.

When cholesterol esterase and cholesterol dehydrogenase are used as enzymes for cholesterol measurement, NAD(P)H is generated from NAD(P) by the enzyme reaction. Cholesterol in small, dense LDL can be quantitatively determined through measurement of the thus generated NAD(P)H at absorbance ranging from 330 nm to 400 nm.

In the step of eliminating cholesterol in L LDL and leading it outside of the reaction system and the step of eliminating cholesterol in lipoproteins other than LDL and leading it outside of the reaction system according to the present invention, a monovalent cation and/or a divalent cation or a salt thereof can be used as an ionic strength adjuster. Addition of such ionic strength adjuster facilitates differentiation of small, dense LDL from L LDL. Specifically, sodium chloride, potassium chloride, magnesium chloride, manganese chloride, calcium chloride, lithium chloride, ammonium chloride, magnesium sulfate, potassium sulfate, lithium sulfate, ammonium sulfate, magnesium acetate, and the like can be used. The concentration of such ionic strength adjuster upon reaction preferably ranges from 0 mmol/L to 100 mmol/L.

Moreover in the present invention, polyanion can also be added in the step of eliminating cholesterol in L LDL and leading it outside of the reaction system and the step of eliminating cholesterol in lipoproteins other than LDL and leading it outside of the reaction system, in order to adjust the catalytic activity of phospholipase against small, dense LDL and L LDL. As polyanion to be added, heparin, phosphotungstic acid, dextran sulfate, or the like can be appropriately used. In the case of heparin, the concentration of polyanion in a reagent preferably ranges from 10 U/mL to 250 U/mL, in the case of phosphotungstic acid, the same preferably ranges from 0.02% (w/v) to 1.25% (w/v), and in the case of dextran sulfate, the same preferably ranges from 0.02% (w/v) to 1.25% (w/v). The concentrations of these polyanions in reaction solutions preferably range from 5 U/mL to 250 U/mL, 0.01% (w/v) to 1.25% (w/v), and 0.01% (w/v) to 1.25% (w/v), respectively.

The reaction in each step of the present invention is preferably carried out at a temperature between 2° C. and 45° C. and further preferably between 25° C. and 40° C.

The reaction in each step is preferably carried out for 1 to 10 minutes and more preferably for 3 to 7 minutes.

Serum and blood plasma can be used as samples in the present invention. However, examples thereof are not limited thereto.

Examples of an autoanalyzer to be used in the present invention include TBA-120FR.200FR (TOSHIBA Corporation), JCA-BM 1250.1650.2250 (JEOL Ltd.), HITACHI7180.7170 (Hitach, Ltd.), and AU2700 (OLYMPUS).

When the measurement method of the present invention is carried out, reagents to be used herein may be divided into a plurality of reagent compositions. Examples of reagents to be used in the present invention include surfactants that react with lipoproteins such as VLDL and HDL other than L LDL and LDL, enzymes for cholesterol measurement such as cholesterol esterase and cholesterol oxidase, surfactants, catalase that degrades hydrogen peroxide, peroxidase for the formation of a dye from hydrogen peroxide via coupling reaction, a hydrogen donor, and a buffer. Division of these reagents into different reagent compositions is adequately performed in view of stability and the like of the reagents. The number of reagent compositions to be used herein may be determined according to the number of the steps of the method of the present invention. For example, when 3 steps are present including the step of eliminating cholesterol in L LDL and leading it outside of the reaction system, the step of eliminating cholesterol in lipoproteins other than LDL and leading it outside of the reaction system, and the step of measuring small, dense LDL, 3 types of reagent composition are prepared to carry out each step. Also, the step of eliminating cholesterol in L LDL and leading it outside of the reaction system and the step of eliminating cholesterol in lipoproteins other than LDL and leading it outside of the reaction system are carried out simultaneously, 2 types of reagent composition are prepared; that is, a reagent composition for carrying out this combined step and a reagent composition for carrying out the step of measuring small, dense LDL are prepared.

In the case of 3 steps, the step of eliminating cholesterol in lipoproteins other than LDL and leading it outside of the reaction system, the step of eliminating cholesterol in L LDL and leading it outside of the reaction system, and the step of measuring small, dense LDL, reagent composition A (reagent composition for eliminating cholesterol in lipoproteins other than LDL), reagent composition B (reagent composition for eliminating cholesterol in L LDL), and reagent composition C (reagent composition for measuring small, dense LDL) are used, respectively. The reagent composition A to be used in the step of eliminating cholesterol in lipoproteins other than LDL and leading it outside of the reaction system contains at least a surfactant such as a polyoxyethylene derivative that acts on lipoproteins such as VLDL and HDL other than LDL. The reagent composition B to be used in the step of eliminating cholesterol in L LDL and leading it outside of the reaction system contains at least phospholipase that reacts with L LDL. The reagent composition A or the reagent composition B, which is added to the initial step, may further contain an enzyme that degrades cholesterol, such as cholesterol esterase or cholesterol oxidase, a hydrogen donor such as an aniline derivative, catalase that eliminates hydrogen peroxide, and the like. For example, when first the step of eliminating cholesterol in lipoproteins other than LDL and leading it outside of the reaction system is carried out and then the step of eliminating cholesterol in L LDL and leading it outside of the reaction system is carried out, the reagent composition A contains at least a surfactant such as a polyoxyethylene derivative that acts on lipoproteins such as VLDL and HDL other than LDL and further contains an enzyme that degrades cholesterol, such as cholesterol esterase or cholesterol oxidase, a hydrogen donor such as an aniline derivative, and catalase that eliminates hydrogen peroxide, for example. The reagent composition B contains at least phospholipase that reacts with L LDL and if necessary a surfactant may be added thereto. On the other hand, when the step of eliminating cholesterol in L LDL and leading it outside of the reaction system is carried out first and then the step of eliminating cholesterol in lipoproteins other than LDL and leading it outside of the reaction system is carried out, the reagent composition B contains at least phospholipase that reacts with L LDL and further contains an enzyme that degrades cholesterol, such as cholesterol esterase and cholesterol oxidase, a hydrogen donor such as an aniline derivative, and catalase that eliminates hydrogen peroxide, for example. The reagent composition A contains at least a surfactant such as a polyoxyethylene derivative that acts on lipoproteins such as VLDL and HDL other than LDL. The reagent composition C to be used in the step of measuring small, dense LDL may contain a surfactant that reacts with only small, dense LDL or a surfactant that acts on all lipoproteins, a hydrogen receptor such as 4 aminoantipyrine, peroxidase, and the like. At this time, a monovalent cation, a divalent cation, or a salt thereof, or polyanion may also be added to the reagent composition A and the reagent composition B, if necessary. Also, the reagent composition A and the reagent composition B may contain serum albumin. The pH of each reagent composition may be around neutral pH and ranges from pH6 to pH8 and preferably ranges from pH6.5 to pH7.5, for example. The pH may be adjusted by addition of a buffer.

When the 3 steps of the method of the present invention are carried out in order of the step of eliminating cholesterol in lipoproteins other than LDL and leading it outside of the reaction system, the step of eliminating cholesterol in L LDL and leading it outside of the reaction system, and the step of measuring small, dense LDL, the reagent composition A is added to a sample for reaction, the reagent composition B is added for reaction, the reagent composition C is added for reaction, and then absorbance is measured.

The amount of a sample and the amount of each reagent composition are not particularly limited and can be adequately determined in view of the concentration or the like of a reagent in each reagent composition. For example, 1 μL to 10 μL of a sample and 25 μL to 200 μL each of the reagent compositions A to C may be used.

When the 3 steps of the method of the present invention are carried out in order of the step of eliminating cholesterol in L LDL and leading it outside of the reaction system, the step of eliminating cholesterol in lipoproteins other than LDL and leading it outside of the reaction system, and the step of measuring small, dense LDL, first the reagent composition B is added to a sample for reaction, subsequently the reagent composition A is added for reaction, the reagent composition C is added for reaction, and then finally absorbance is measured.

In the method of the present invention, cholesterol in L LDL and cholesterol in lipoproteins other than LDL are led outside of the reaction system in advance of the step of measuring small, dense LDL, so that small, dense LDL can be measured. As a method to lead cholesterol in L LDL and cholesterol in lipoproteins other than LDL outside of the reaction system, known techniques for aggregation, inhibition, and the like can be employed, in addition to elimination as described above. Also, when two or more steps are carried out before the step of measuring small, dense LDL, a reaction to lead cholesterol in L LDL and cholesterol in lipoproteins other than LDL outside of the reaction system may be completed in a step immediately before the step of measuring small, dense LDL. Accordingly, it is also possible to cause phospholipase to act on cholesterol in L LDL in one step, followed by elimination in the subsequent step. Alternatively, it is possible to degrade cholesterol in lipoproteins other than LDL in one step, followed by elimination in the subsequent step, for example. The products of each step can also be eliminated in the same step.

The step of eliminating cholesterol in lipoproteins other than LDL and leading it outside of the reaction system and the step of eliminating cholesterol in L LDL and leading it outside of the reaction system may be combined to be a single step. When a reaction is conducted by the 2 steps comprising the single step and the subsequent step of measuring small, dense LDL, a reagent composition AB (containing reagents contained in the above reagent composition A and reagent composition B) and the reagent composition C may be used in the first step. Specifically, the reagent composition AB contains at least a surfactant such as a polyoxyethylene derivative that acts on lipoproteins such as VLDL and HDL other than LDL and phospholipase that reacts with L LDL. In this case, the reagent composition AB is added to a sample, lipoproteins such as VLDL and HDL other than L LDL and LDL are caused to act on a surfactant, the resultant is reacted with an enzyme, subsequently the reagent composition C is added to cause small, dense LDL to act on a surfactant for reaction with an enzyme, and then cholesterol in small, dense LDL is measured.

EXAMPLES

Hereafter, the present invention is described in greater detail with reference to the following examples, although the present invention is not limited thereto.

Example 1

The step of eliminating cholesterol in lipoproteins other than LDL, the step of eliminating cholesterol in L LDL, and the step of measuring small, dense LDL cholesterol were carried out in this order, and then small, dense LDL were measured.

The reagent composition A to be used in the step of eliminating cholesterol in lipoproteins other than LDL, the reagent composition B to be used in the step of eliminating cholesterol in L LDL, and the reagent composition C to be used in the step of measuring small, dense LDL cholesterol were prepared as follows.

Reagent Composition A

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| Bovine serum albumin | 0.5% (w/v) |
| TOOS | 2.0 mmol/L |
| Polyoxyethylene derivative [Kao Corporation, EMULGEN B-66] | 0.27% (w/v) |
| Polyoxyethylene distyrenated phenyl ether [Kao Corporation, EMULGEN A-90] | 0.03% (w/v) |

Reagent Composition B

| | |
|---|---|
| PIPES buffer, pH 7.0 | 50 mmol/L |
| Phospholipase A2 [Asahi Kasei Corporation, PLA2] | 11.0 U/mL |
| Calcium chloride | 100 mmol/L |

Reagent Composition C

| | |
|---|---|
| PIPES buffer, pH7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation EMULGEN 909] | 1.0% (w/v) |

The reagent composition A (75 μL) was added to 2 μL of a serum sample, followed by 5 minutes of reaction at 37° C. The reagent composition B (75 μL) was added, followed by 5 minutes of reaction. Then the reagent composition C (50 μL)

was added, followed by 5 minutes of reaction. Absorbance was measured at a dominant wavelength of 600 nm and a subwavelength of 700 nm.

Figure 1:
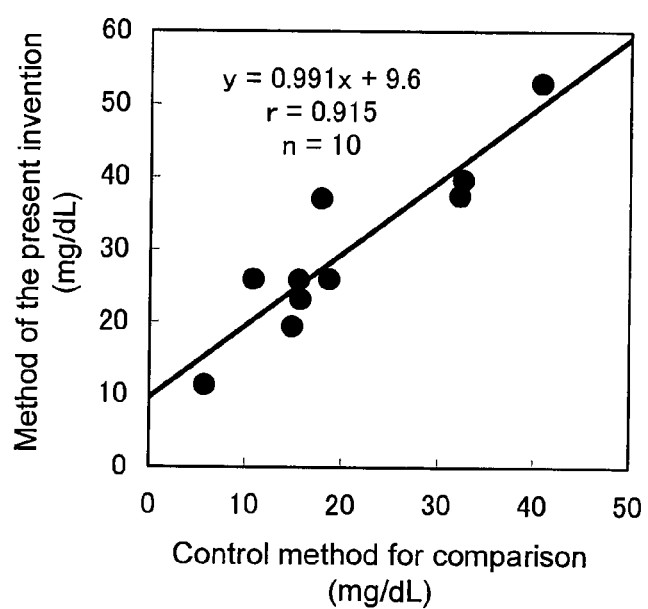
FIG. 1 shows the correlation between:
the method of the present invention, which comprises 3 steps wherein the first step is a step of eliminating cholesterol in lipoproteins other than LDL so as to lead the cholesterol outside of the reaction system and use phospholipase A2 as phospholipase; and a method using a sd LDL-C "SEIKEN" reagent for measurement of small, dense LDL cholesterol.

A sd LDL-C "SEIKEN" reagent for measurement of small, dense LDL cholesterol (DENKA SEIKEN Co., Ltd.) was used in a control method for comparison and then small, dense LDL cholesterol concentrations were compared. FIG. 1 shows the results.

As shown in FIG. 1, the method of this Example exhibited good correlation with the method using the sd LDL-C "SEIKEN" reagent for measurement of small, dense LDL cholesterol.

Example 2

A reagent composition was prepared from the reagent composition B used in Example 1, containing phospholipase C [PLC] as phospholipase.

Reagent Composition A

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| TOOS | 2.0 mmol/L |
| Polyoxyethylene derivative [Kao Corporation, EMULGEN B-66] | 0.27% (w/v) |
| Polyoxyethylene distyrenated phenyl ether [Kao Corporation, EMULGEN A-90] | 0.03% (w/v) |

Reagent Composition B

| | |
|---|---|
| PIPES buffer, pH 7.0 | 50 mmol/L |
| Phospholipase C [Asahi Kasei Corporation, PLC] | 1.16 U/mL |

Reagent Composition C

| | |
|---|---|
| PIPES buffer, pH7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 909] | 1.0% (w/v) |

Figure 2:
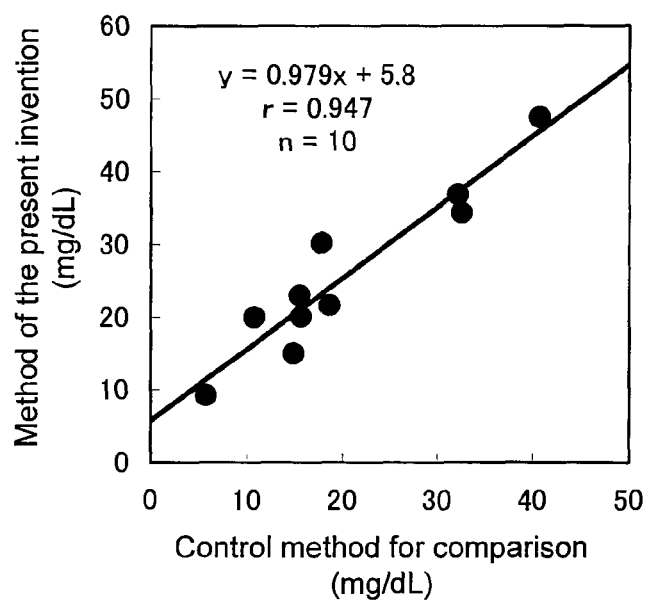

Measurement was carried out in a manner similar to that in Example 1. The results were compared with those obtained with the use of the sd LDL-C "SEIKEN" reagent. FIG. 2 shows the results.

As shown in FIG. 2, the method of the Example exhibited good correlation with the method using the sd LDL-C "SEIKEN" reagent for measurement of small, dense LDL cholesterol.

Example 3

A reagent composition was prepared from the reagent composition B used in Example 1, containing phospholipase D [PLD] as phospholipase.

Reagent Composition A

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| TOOS | 2.0 mmol/L |
| Polyoxyethylene derivative [Kao Corporation, EMULGEN B-66] | 0.27% (w/v) |
| Polyoxyethylene distyrenated phenyl ether [Kao Corporation, EMULGEN A-90] | 0.03% (w/v) |

Reagent Composition B

| | |
|---|---|
| PIPES buffer, pH 7.0 | 50 mmol/L |
| Phospholipase D [Asahi Kasei Corporation, PLD] | 1.36 U/mL |
| Calcium chloride | 1.0 mmol/L |

Reagent Composition C

| | |
|---|---|
| PIPES buffer, pH 7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 909] | 1.0% (w/v) |

Measurement was carried out in a manner similar to that in Example 1. The results were compared with those obtained with the use of the sd LDL-C "SEIKEN" reagent. FIG. 3 shows the results.

As shown in FIG. 3, the method of the Example exhibited good correlation with the method using the sd LDL-C "SEIKEN" reagent for measurement of small, dense LDL cholesterol.

Example 4

A reagent composition was prepared from the reagent composition B used in Example 1, containing lysophospholipase [LYPL] as phospholipase.

Reagent Composition A

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| TOOS | 2.0 mmol/L |
| Polyoxyethylene derivative [Kao Corporation, EMULGEN B-66] | 0.27% (w/v) |
| Polyoxyethylene distyrenated phenyl ether [Kao Corporation, EMULGEN A-90] | 0.03% (w/v) |

Reagent Composition B

| | |
|---|---|
| PIPES buffer,, pH 7.0 | 50 mmol/L |
| lysophospholipase [Asahi Kasei Corporation, LYPL] | 1.18 U/mL |
| Calcium chloride | 2.0 mmol/L |

Reagent Composition C

| | |
|---|---|
| PIPES buffer, pH 7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 909] | 1.0% (w/v) |

Measurement was carried out in a manner similar to that in Example 1. The results were compared with those obtained with the use of the sd LDL-C "SEIKEN" reagent. FIG. 4 shows the results.

As shown in FIG. 4, the method of the Example exhibited good correlation with the method using the sd LDL-C "SEIKEN" reagent for measurement of small, dense LDL cholesterol.

Example 5

A reagent composition was prepared from the reagent composition B used in Example 1, containing phospholipase [PLDP] specific to glycerophospholipid, as phospholipase.

Reagent Composition A

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| TOOS | 2.0 mmol/L |
| Polyoxyethylene derivative [Kao Corporation, EMULGEN B-66] | 0.27% (w/v) |
| Polyoxyethylene distyrenated phenyl ether [Kao Corporation, EMULGEN A-90] | 0.03% (w/v) |

Reagent Composition B

| | |
|---|---|
| PIPES buffer, pH 7.0 | 50 mmol/L |
| Phospholipase [Asahi Kasei Corporation, PLDP] | 7.5 U/mL |

Reagent Composition C

| | |
|---|---|
| PIPES buffer, pH7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 909] | 1.0% (w/v) |

Measurement was carried out in a manner similar to that in Example 1. The results were compared with those obtained with the use of the sd LDL-C "SEIKEN" reagent. FIG. 5 shows the results.

As shown in FIG. 5, the method of the Example exhibited good correlation with the method using the sd LDL-C "SEIKEN" reagent for measurement of small, dense LDL cholesterol.

Example 6

A reagent composition was prepared from the reagent composition B used in Example 1, containing sphingomyelinase [SPC] as phospholipase.

Reagent Composition A

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| TOOS | 2.0 mmol/L |
| Polyoxyethylene derivative [Kao Corporation, EMULGEN B-66] | 0.27% (w/v) |
| Polyoxyethylene distyrenated phenyl ether [Kao Corporation, EMULGEN A-90] | 0.03% (w/v) |

Reagent Composition B

| | |
|---|---|
| PIPES buffer, pH 7.0 | 50 mmol/L |
| Sphingomyelinase [Asahi Kasei Corporation, SPC] | 0.97 U/mL |

Reagent Composition C

| | |
|---|---|
| PIPES buffer, pH 7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 909] | 1.0% (w/v) |

Measurement was carried out in a manner similar to that in Example 1. The results were compared with those obtained with the use of the sd LDL-C "SEIKEN" reagent. FIG. 6 shows the results.

As shown in FIG. 6, the method of the Example exhibited good correlation with the method using the sd LDL-C "SEIKEN" reagent for measurement of small, dense LDL cholesterol.

Example 7

The step of eliminating cholesterol in L LDL, the step of eliminating cholesterol in lipoproteins other than LDL, and the step of measuring small, dense LDL cholesterol were carried out in this order, and then small, dense LDL were measured.

The reagent composition B to be used in the step of eliminating cholesterol in L LDL, the reagent composition A to be used in the step of eliminating cholesterol in lipoproteins other than LDL, and the reagent composition C to be used in the step of measuring small, dense LDL cholesterol were prepared as follows.

Reagent Composition B

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| Bovine serum albumin | 0.5% (w/v) |
| TOOS | 2.0 mmol/L |
| Sphingomyelinase [Asahi Kasei Corporation, SPC] | 0.485 U/mL |

Reagent Composition A

| | |
|---|---|
| PIPES buffer, pH 7.0 | 50 mmol/L |
| Polyoxyethylene distyrenated phenyl ether [Kao Corporation, EMULGEN A-90] | 0.6% (w/v) |

Reagent Composition C

| | |
|---|---|
| PIPES buffer, pH7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 909] | 1.0% (w/v) |

The reagent composition B (75 μL) was added to 2 μL of a serum sample, followed by 5 minutes of reaction at 37° C. The reagent composition A (75 μL) was added, followed by 5 minutes of reaction. Then the reagent composition C (50 μL) was added, followed by 5 minutes of reaction. Absorbance was measured at a dominant wavelength of 600 nm and a subwavelength of 700 nm.

A sd LDL-C "SEIKEN" reagent for measurement of small, dense LDL cholesterol (DENKA SEIKEN Co., Ltd.) was used in a control method for comparison and then small, dense LDL cholesterol concentrations were compared. FIG. 7 shows the results.

As shown in FIG. 7, the method of this Example exhibited good correlation with the method using the sd LDL-C "SEIKEN" reagent for measurement of small, dense LDL cholesterol.

Example 8

In this Example, the step of eliminating cholesterol in L LDL and the step of eliminating cholesterol in lipoproteins other than LDL (that is, the step of eliminating cholesterol in those other than small, dense LDL) were carried out simultaneously. A reagent composition AB to be used in the step of eliminating LLDL and the step of eliminating lipoproteins other than LDL (that is, the step of eliminating those other than small, dense LDL) and the reagent composition C to be used in the step of measuring small, dense LDL cholesterol were prepared as follows.

Reagent Composition AB

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| Bovine serum albumin | 0.5% (w/v) |
| TOOS | 2.0 mmol/L |
| Sphingomyelinase [Asahi Kasei Corporation, SPC] | 1.46 U/mL |
| Polyoxyethylene derivative [Kao Corporation, EMULGEN B-66] | 0.135% (w/v) |
| Polyoxyethylene distyrenated phenyl ether [Kao Corporation, EMULGEN A-90] | 0.015% (w/v) |

Reagent Composition C

| | |
|---|---|
| PIPES buffer, pH 7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 909] | 1.0% (w/v) |

The reagent composition AB (150 μL) was added to 2 μL of a serum sample, followed by 5 minutes of reaction at 37° C. The reagent composition C (50 μL) was then added, followed by 5 minutes of reaction. Absorbance was measured at a dominant wavelength of 600 nm and a subwavelength of 700 nm.

A sd LDL-C "SEIKEN" reagent for measurement of small, dense LDL cholesterol (DENKA SEIKEN Co., Ltd.) was used in a control method for comparison and then small, dense LDL cholesterol concentrations were compared. FIG. 8 shows the results.

As shown in FIG. 8, the method of this Example exhibited good correlation with the method using the sd LDL-C "SEIKEN" reagent for measurement of small, dense LDL cholesterol.

Example 9

A reagent composition was prepared from the reagent composition A used in Example 6, containing a single type of surfactant, EMULGEN B-66.

Reagent Composition A

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| TOOS | 2.0 mmol/L |
| Polyoxyethylene derivative [Kao Corporation, EMULGEN B-66] | 0.27% (w/v) |

Reagent Composition B

| | |
|---|---|
| PIPES buffer, pH 7.0 | 50 mmol/L |
| Sphingomyelinase [Asahi Kasei Corporation, SPC] | 0.97 U/mL |

Reagent Composition C

| | |
|---|---|
| PIPES buffer, pH7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 909] | 1.0% (w/v) |

Measurement was carried out in a manner similar to that in Example 1. The results were compared with those obtained using a sd LDL-C "SEIKEN" reagent. FIG. 9 shows the results.

As shown in FIG. 9, the method of this Example exhibited good correlation with the method using the sd LDL-C "SEIKEN" reagent for measurement of small, dense LDL cholesterol.

Example 10

A reagent composition was prepared from the reagent composition AB, containing a single type of surfactant, EMULGEN A-90.

Reagent Composition AB

| | |
|---|---|
| PIPES buffer, pH 7.0 | 50 mmol/L |
| Cholesterol esterase | 1.2 U/mL |
| Cholesterol oxidase | 0.3 U/mL |
| Catalase | 1200 U/mL |
| Bovine serum albumin | 1.0% (w/v) |
| TOOS | 2.0 mmol/L |
| Sphingomyelinase [Asahi Kasei Corporation, SPC] | 3.0 U/mL |
| Polyoxyethylene distyrenated phenyl ether [Kao Corporation, EMULGEN A-90] | 0.18% (w/v) |

Reagent Composition C

| | |
|---|---|
| PIPES buffer, pH 7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 709] | 1.0% (w/v) |

The reagent composition AB (150 μL) was added to 2 μL of a serum sample, followed by 5 minutes of reaction at 37° C. The reagent composition C (50 μL) was then added, followed by 5 minutes of reaction. Absorbance was measured at a dominant wavelength of 600 nm and a subwavelength of 700 nm.

An ultracentrifugation method was employed for comparison. FIG. 10 shows the results.

As shown in FIG. 10, the method of this Example exhibited good correlation with the method using the sd LDL-C "SEIKEN" reagent for measurement of small, dense LDL cholesterol.

Example 11

A reagent composition was prepared from the reagent composition AB, containing no surfactant used therein.

Reagent Composition AB

| | |
|---|---|
| PIPES buffer, pH 7.0 | 50 mmol/L |
| Cholesterol esterase | 0.6 U/mL |
| Cholesterol oxidase | 0.3 U/mL |
| Catalase | 1200 U/mL |
| Bovine serum albumin | 1.0% (w/v) |
| TOOS | 2.0 mmol/L |
| Sphingomyelinase [Asahi Kasei Corporation, SPC] | 1.6 U/mL |

Reagent Composition C

| | |
|---|---|
| PIPES buffer, pH 7.0 | 50 mmol/L |
| 4-aminoantipyrine | 4.0 mmol/L |
| Peroxidase | 4.0 units/mL |
| Sodium azide | 0.05% (w/v) |
| Polyoxyethylenenonylphenyl ether [Kao Corporation, EMULGEN 709] | 1.0% (w/v) |

The reagent composition AB (150 µL) was added to 2 µL of a serum sample, followed by 5 minutes of reaction at 37° C. The reagent composition C (50 µL) was then added, followed by 5 minutes of reaction. Absorbance was measured at a dominant wavelength of 600 nm and a subwavelength of 700 nm.

An ultracentrifugation method was employed for comparison. FIG. 11 shows the results.

As shown in FIG. 11, the method of this Example exhibited good correlation with the method using the sd LDL-C "SEIKEN" reagent for measurement of small, dense LDL cholesterol.

Example 12

Reagents were prepared from the reagent composition A used in Example 1 through addition of various surfactants. A surfactant added herein was NONION HS215, EMULGEN 920, NONION NS220, NONION HS220, NONION NS230, or PERSOFT EP. NONION HS215, EMULGEN 920, or NONION NS220 was added at 0.03% (w/v). NONION HS220, NONION NS230, or PERSOFT EP was added at 0.06% (w/v).

Reagent Composition A

| | |
|---|---|
| PIPES buffer, pH 7.0 | 50 mmol/L |
| Cholesterol esterase | 0.6 U/mL |
| Cholesterol oxidase | 0.5 U/mL |
| Catalase | 600 U/mL |
| TOOS | 2.0 mmol/L |
| Various surfactants | |
| EMULGEN B-66 | 0.27% (w/v) |
| NONION HS215, EMULGEN 920, NONION NS220, | 0.03% (w/v) (NONION HS215, EMULGEN 920, NONION NS220) or |
| NONION HS220, NONION NS230, or PERSOFT EP | 0.06% (w/v) (NONION HS220, NONION NS230, PERSOFT EP) |

Reagent Composition B

| | |
|---|---|
| PIPES buffer, pH 7.0 | 50 mmol/L |
| Sphingomyelinase [Asahi Kasei Corporation, SPC] | 0.97 U/mL |

Reagent Composition C

| | |
|---|---|
| PIPES buffer, pH 7.0 | 50 mmol/L |
| 4-aminoantipyrine | 4.0 mmol/L |
| Proxidase | 4.0 units/mL |
| Sodium azide | 0.05% (w/v) |
| Polyoxyethylenenonylphenyl ether [Kao Corporation, EMULGEN 909] | 1.0% (w/v) |

Measurement was carried out in a manner similar to that in Example 1. The results were compared with those obtained using a sd LDL-C "SEIKEN" reagent. Table 1 shows the results.

As shown in Table 1, the method of this Example exhibited good correlation with the method using the sd LDL-C "SEIKEN" reagent for measurement of small, dense LDL cholesterol.

As shown in Table 1, the method using the reagent composition A containing as surfactants EMULGEN B-66 and NONION HS215, EMULGEN 920, NONION NS220, NONION HS220, NONION NS230, or PERSOFT EP in combination exhibited good correlation with the method using the sd LDL-C "SEIKEN" reagent for measurement of small, dense LDL cholesterol.

TABLE 1

| Surfactant | n | | Correlation coefficient |
|---|---|---|---|
| EMULGEN B-66 NONION HS215 | 11 | y = 1.0889x − 0.3865 | r = 0.920 |
| EMULGEN B-66 EMULGEN 920 | 11 | y = 0.9546x + 4.0194 | r = 0.927 |
| EMULGEN B-66 NONION NS220 | 11 | y = 0.9751x + 4.5445 | r = 0.928 |
| EMULGEN B-66 NONION HS220 | 11 | y = 0.9863x + 9.4759 | r = 0.898 |
| EMULGEN B-66 NONION NS230 | 11 | y = 0.9832x + 9.3521 | r = 0.915 |
| EMULGEN B-66 PERSOFT EP | 11 | y = 0.9857x − 0.6354 | r = 0.930 |

All publications, patents, and patent applications cited herein are incorporated herein by reference in their entirety.

The invention claimed is:
1. A kit for quantitatively determining small, dense LDL cholesterol, comprising:
   (i) a reagent composition for eliminating cholesterol in LDL other than small, dense LDL in a sample, containing at least sphingomyelinase that reacts with LDL other than small, dense LDL; and
   (ii) a reagent composition for measurement of small, dense LDL, containing:
      (a) a surfactant that is a polyoxyethylene-polyoxypropylene copolymer that reacts with only small, dense

LDL or a derivative thereof; or a surfactant that is a polyoxyethylene derivative with HLB of 11 or more and less than 14;
(b) 4 aminoantipyrine; and
(c) peroxidase.

2. The kit according to claim 1, further comprising (iii) a reagent composition for eliminating cholesterol in lipoproteins other than LDL, said reagent containing:
(a) a nonionic surfactant selected from the group consisting of at least polyoxyethylene alkyl ether, polyoxyethylene alkyl phenyl ether, and polyoxyethylene alkyl amine;
(b) an anionic surfactant selected from the group consisting of polyoxyethylene alkylether sulfate, alkyl sulfate, amide ether sulfate, alkyl taurate, and a phosphate-type surfactant;
(c) a cationic surfactant selected from the group consisting of an alkyl methyl ammonium salt, a quaternary ammonium salt, and a mono-linear alkyl type surfactant; or
(d) an amphoteric surfactant selected from the group consisting of lauryl betaine, dimethyl alkyl betaine, an imidazoline type surfactant, and sodium alkyldiaminoethyl glycine.

3. The kit according to claim 1, wherein the reagent composition (i) further comprises:
(a) a nonionic surfactant selected from the group consisting of at least polyoxyethylene alkyl ether, polyoxyethylene alkyl phenyl ether, and polyoxyethylene alkyl amine;
(b) an anionic surfactant selected from the group consisting of polyoxyethylene alkylether sulfate, alkyl sulfate, amide ether sulfate, alkyl taurate, and a phosphate-type surfactant;
(c) a cationic surfactant selected from the group consisting of an alkyl methyl ammonium salt, a quaternary ammonium salt, and a mono-linear alkyl type surfactant; or
(d) an amphoteric surfactant selected from the group consisting of lauryl betaine, dimethyl alkyl betaine, an imidazoline type surfactant, and sodium alkyldiaminoethyl glycine, whereby cholesterol in lipoproteins other than small, dense LDL in a sample is eliminated by the reagent composition (i).

4. The kit according to claim 1, wherein the sphingomyelinase has higher reactivity with at least sphingomyelin than with other phospholipids existing in lipoproteins.

* * * * *